(12) United States Patent
Stimpson

(10) Patent No.: US 6,521,465 B2
(45) Date of Patent: Feb. 18, 2003

(54) PARALLEL PRODUCTION OF HIGH DENSITY ARRAYS

(75) Inventor: Don Stimpson, Garland, TX (US)

(73) Assignee: Unitec Co., Ltd., Tokyo (JP)

( * ) Notice: Subject to any disclaimer, the term of this patent is extended or adjusted under 35 U.S.C. 154(b) by 0 days.

(21) Appl. No.: 09/952,469

(22) Filed: Sep. 14, 2001

(65) Prior Publication Data

US 2002/0076829 A1 Jun. 20, 2002

Related U.S. Application Data

(62) Division of application No. 09/337,594, filed on Jun. 21, 1999, now Pat. No. 6,306,664, which is a continuation of application No. 08/895,117, filed on Jul. 16, 1997, now Pat. No. 6,037,186.

(51) Int. Cl.[7] .................. G01N 33/543; G01N 33/531; C12Q 1/00; B32B 1/08; C12M 3/00
(52) U.S. Cl. ................. 436/518; 436/164; 436/172; 436/513; 436/514; 436/524; 436/527; 436/805; 436/809; 436/823; 435/4; 435/7.1; 435/7.92; 435/174; 435/287.1; 435/287.8; 435/969; 428/36.4; 428/36.9; 428/36.91; 428/373; 401/196
(58) Field of Search .................. 401/196; 428/36.9, 428/36.4, 36.91, 373; 435/4, 7.1, 7.92, 174, 287.1, 287.8, 969; 436/164, 172, 805, 823, 513, 518, 514, 524, 527, 809

(56) References Cited

U.S. PATENT DOCUMENTS

| 4,591,570 A | 5/1986 | Chang ................. 436/518 |
| 5,126,643 A | 6/1992 | French ................. 318/434 |
| 5,175,209 A | 12/1992 | Beattie et al. .......... 525/54.11 |
| 5,202,231 A | 4/1993 | Drmanac et al. ............ 435/6 |
| 5,244,636 A | 9/1993 | Walt et al. ............. 422/82.07 |
| 5,298,741 A * | 3/1994 | Walt et al. ............ 250/227.21 |
| 5,320,814 A * | 6/1994 | Walt et al. ................ 385/12 |
| 5,387,790 A | 2/1995 | Stimpson ............. 250/214 RC |
| 5,449,754 A | 9/1995 | Nishioka ................ 530/334 |
| 5,605,746 A * | 2/1997 | Groeger et al. ............ 428/359 |

FOREIGN PATENT DOCUMENTS

WO    WO 95/11755 A1 * 5/1995

OTHER PUBLICATIONS

Disclosure Document No. 409060 entitled "Method of Combinatorial Synthesis to Produce Two Dimensions High Density Arrays for Diagnostic Testing" dated Nov. 16, 1996.
Disclosure Document No. 379155 entitled "Method of Combinatorial Synthesis to Produce High Density Arrays for Diagnostic Testing" dated Mar. 22, 1996.

* cited by examiner

Primary Examiner—Christopher L. Chin
Assistant Examiner—Kartic Padmanabhan
(74) Attorney, Agent, or Firm—Haynes and Boone, LLP

(57) ABSTRACT

An array bundle is provided for creating multiple arrays for testing. The array bundle is adapted to be cut transversely to form a series of identical arrays of cells. In one embodiment, the array bundle is used in detecting predetermined components from sample mixtures.

5 Claims, 6 Drawing Sheets

PARALLEL PRODUCTION OF HIGH DENSITY ARRAYS

CROSS REFERENCE

This application is a Divisional of U.S. application Ser. No. 09/337,594, filed on Jun. 21, 1999 now U.S. Pat. No. 6,306,664 which is a Continuation of U.S. application Ser. No. 08/895,117 Pat. No. 6,037,186, filed Jul. 16, 1997 and issued on Mar. 14, 2000.

BACKGROUND OF THE INVENTION

1. Field of the Invention

The invention is a method for producing and/or using arrays which contain a multiplicity of compounds for the purpose of screening to identify molecules with desirable properties. The various compounds forming the elements of the array can be synthesized in place using combinatorial synthesis schemes, or pre-synthesized compounds can be incorporated into the array. Applications to genetic screening, in vitro diagnostics, and drug discovery are anticipated.

2. Discussion of the Prior Art

Current trends in medical diagnostic testing and pharmaceutical research are toward conducting a large number of tests concurrently on a single device. For example, one such device has been called a DNA "chip" for sequence analysis. A DNA chip contains a large number (thousands) of unique DNA molecules (probes) immobilized on a flat surface in the form of an array (e.g. checker board). The company Affymax uses a photo-lithographic method to produce DNA chips (Fodor, S.P.A., et.al., Science, 1991, 251, 767–773). Another approach is to use pre-synthesized molecules which are applied and immobilized to a suitable substrate (e.g. microporous membrane).

For example, an unknown sample of DNA (target) is applied to the chip and a hybridization pattern is formed. The pattern is indicative of the strength of interaction between the target DNA and the various immobilized probes and can yield sequence information. When the sequence of the target DNA is not known the technology is generally referred to as sequencing by hybridization (SBH) as described in U.S. Pat. No. 5,202,231. In other applications where the sequence of the target is known and detection is directed at identification of a change associated with a disease state the method is commonly referred to as "re-sequencing" or allele specific oligonucleotide hybridization.

Another trend in the arena of pharmaceutical drug discovery is known as combinatorial synthesis. In this case a large number of similar compounds are synthesized and simultaneously screened for the desired biological response, for example binding to a receptor molecule. When one or more candidate compounds in the combinatorial bank are discovered they are synthesized in larger quantities for further testing. Molecules of interest include peptides, nucleic acids as well as drug compounds synthesized by standard organic chemical methods or other novel methods for drug discovery.

Finally, in the area of in vitro diagnostics there is a need for panel assays where several tests are run concurrently on a given sample using an array of immobilized binding agents. An example of such array immunoassay devices is described in U.S. Pat. Nos. 4,591,570 and 4,829,010. Pre-manufactured compounds, such as mono-clonal antibodies, are used to make arrays whose elements have particular binding properties for diagnostic analysis. In principle a patient test sample can be simultaneously analyzed for the presence or absence of several molecules, i.e. analytes. Further, the levels of the various analytes can be measured simultaneously by quantitative analysis of the signals developed at each site of the array. In other applications there is a need for graphic symbols that can be visually analyzed to determine the presence or absence of a single analyte in a patient test sample. For the present invention, the graphic symbol can be thought of as an array of individual elements that are spatially arranged to yield a graphic symbol as a result of the detection process. In this case, the size of the array elements determine the "grain" of the graphic symbol.

Thus, there is a need for methods to produce and concurrently test multiple compounds or binding agents in the form of an array. An additional requirement is the need for high density devices (i.e. high spatial density) so that the large numbers of compounds are presented in a package of reasonable size. For example, a device that contains a possible 8-mer DNA sequences composed of the 4 DNA bases, A (adenine), T (thymine), G (guanine) and C (cytosine) requires $4^8$=65536 different compounds. If each element (i.e. a zone of immobilized binding agent) was a square only 1 millimeter (1 mm=0.1 cm) in size, an array of 65536 elements would be 10 inches on a side. Clearly, such devices would be difficult to manipulate and would require relatively large amounts of the test sample to be spread evenly over the array surface. A 0.1 mm thick layer of test sample spread on a 10×10 inch area amounts to about 6.5 ml (ml=milliliter=6.5×10-3 liter). Since most test samples are of biological origin, they are typically very expensive, difficult to prepare and in short supply. Examples of test samples are PCR products or purified drug receptors which are typically available in microliter quantities-1000 times less than in the above example. In most cases, DNA synthesis requires the use of expensive components, phosphoramidite DNA synthesis being a case in point, so surface area of the array is also important during the manufacturing step.

Thus, the smaller the size of the array elements involved in the synthesis the more economical the device will be to produce and use. Several methods exist to create chips with large numbers of different sequences but often result in devices with large features, large physical size and, hence, low spatial density. For example, one method uses disks or channels to produce arrays of probe DNA's using standard DNA synthesis chemistry (see for example, Williams, et.al., Nucleic Acids Research 1994, 22, 1365 or Southern et.al., Nucleic Acids Research, 1994, 22, 1368 and references therein). The drawback of this method is that small feature size is not obtained.

Another method of making DNA chips is to use pre-synthesized probe DNA's and a printing device to allow application of the various compounds. The probes are applied to the chip with a pin or a pipette in the pattern of an array and immobilized by any of a variety of techniques such as adsorption or covalent linkage. An example of such DNA arrays is described in Stimpson et.al. Proc. Natl. Acad. Sci. USA Vol. 92, pp. 6379–6383, July 1996. Since elements of the array are formed by the application of a DNA solution to the surface of the array the process is relatively slow.

One method to produce high density chips uses photo-lithography (Pease et al., Proc. Natl. Acad. Sci. USA Vol. 91, pp. 5022, 1994). One drawback to this method is that it relies on a new DNA synthesis chemistry as opposed to the standard phosphoramidite chemistry used in commercial DNA synthesizers. The technology feeds off the methods evolved in the electronics industry and therefore has some of the same requirements, vis, accurate positioning to micron scales, clean room requirements and the use of multiple photo-masks to define the array pattern. Although electronic "chips" (for example an Intel PENTIUM® microprocessor) are mass produced economically, they are typically too expensive to be used as a disposable element, as is needed with a DNA chip.

Another drawback of such chips is the use of a solid impermeable support material like a glass slide or cover slip. As a result, only the very small amount of material immobilized on the surface of the solid chip is used to capture target molecules. An improvement is described using porous silicon or channel glass whereby hybridization reactions occur within the three-dimensional volumes of porous silicon dioxide of channel array glass rather than two-dimensional surface areas (Beattie, K. L., The 1994 San Diego Conference: The Genetic Revolution).

Unfortunately, all the array fabrication methods mentioned above suffer from a common limitation, i.e., each element of each array is a unique synthesis or an application step. This is true even when array elements or entire arrays are simply duplicated or produced "in parallel", or more accurately, concurrently. Since each element is a unique synthesis or application there is a chance for variation between corresponding elements on different arrays or, for that matter, duplicated elements on the same array. When multiple arrays are produced concurrently it is carried out in a two dimensional fashion, i.e., arrays are produced next to one another in a two dimensional X-Y plane, where X and Y refer to the two degrees of spatial freedom. In a photo-lithographic process, increasing the number of chips on a wafer (the substrate on which multiple arrays are produced) results in an increase in surface area which increases demand on the chemicals used in photo-chemistry (assuming no change in chip size).

SUMMARY OF THE INVENTION

The object of the present invention is to extend array construction into a third dimension, Z, so that each array element formed by a synthesis or application of a binding agent is used to produce many arrays. Individual arrays are formed by cutting slabs along the Z axis of a bundle assembled from the various array elements.

The present invention forms elements for the construction of two dimensional (X-Y) arrays by synthesis or applications of binding agents in a third or Z dimension. The invention is based on the observation that arrays cut from bundles of porous rods or spiral wound porous sheets behave like membranes composed of said porous materials and conduct flow through the multitude of edges exposed during cutting. Surprisingly, liquid flows substantially through the multiple porous rod or sheets which comprise the array and not through the intervening spaces between the array elements.

In one embodiment, the elements of the array are formed by the ends of rods of porous materials which are compatible with a chemical synthesis or compound application step. For application of protoinaccous (e.g. antibodies) or nucleic acid (e.g. derived from a cDNA library) compounds the porous matrix can be selected from any of the materials currently used to produce microporous membranes by a phase inversion or a leaching process. Examples of suitable microporous membrane materials are cellulose, nitrocellulose, polysulfone, nylon, polypropylene or glass. (For a discussion on methods of producing microporous polymer membranes see Synthetic Polymeric Membranes, R. E. Kesting, John Wiley & Sons, 1985, ISBN 0471-807176. For a discussion on methods of producing porous glass materials see Solid Phase Biochemistry, W. E. Scouten Ed., John Wiley & Sones, 1983, ISBN 0471-08585-5, Chapter 11, Application of Controlled Pore Glass in Solid Phase Biochemistry by W. Haller). In particular, nitrocellulose is preferred for protein components while nylon is preferred for immobilization of nucleic acid compounds. In each case, rods or "threads" of such materials can be formed from processes similar to those used in producing hollow fiber membranes or flat sheet membranes. Alternatively, materials that are commonly used for producing "threads" or "yarns" by a spinning process can be utilized to make rods, for example, polyester thread. Each rod is dipped or otherwise exposed to a unique binding agent to allow uniform attachment throughout its length (Z axis). The attachment procedure may involve simple adsorption, covalent attachment chemistries, multiple washing or adsorption steps or other manipulations to achieve the desired properties of the particular array element. For a complete discussion on methods of covalent attachment to various solid supports see Pierce Catalog and Handbook, 1994. Synthesis steps on the rods elements may involve standard DNA synthesis chemistries or other synthetic methods of organic chemistry to achieve the desired spectrum of molecules for screening as used in drug discovery or gene identification. It is important to note that the binding agent is introduced to the array element in a batch mode, i.e., the entire rod is treated uniformly. The array elements can be subjected to a quality control step before assembly into the bundle used to make the arrays. When all array elements are available they ere formed into a rod bundle using radial compression about the Z axis of the bundle. The rods may be organized in the bundle by using a guide, i.e., a plate with a series of holes to direct the rods to a particular point of the array. The bundle can be compressed by pulling it through a cone shaped guide. A sheath is wrapped around the bundle, as in the insulation around a bundle of conducting electrical wires, to hold the elements in place. The resulting rod bundle is then sliced into multiple arrays along the Z axis. Each array consists of a two dimensional arrangement of rod elements with the various compounds displayed on the newly cut ends of each rod. Hence, each synthesis or application step to produce a given array element is used to produce many arrays. Uniformity of binding agent is anticipated for a given batch of arrays because any given element is produced by a single synthesis or application step. This is opposed to prior art where each element is produce by a unique application or synthesis, even when said reactions are carried out in parallel. Another interesting feature of the method is that array density is determined by the diameter of the rod elements and is not limited by the density of the reagent application or synthesis (e.g. ink jet or photo-lithography).

In some cases it may be desirable to arrange particular rod elements in the form a graphic symbol within the array. To form a graphic symbol from rod elements a guide device would be used to direct each rod element to the correct position in the array to form the graphic symbol. For a graphic symbol large enough to be read by the human eye, multiple rods with the same binding properties are used. The diameter of the rods at the edge of the symbol determines the grain or pixel density of the final graphic. For a production process, each rod element is stockpiled on a spool. The spools are dipped or otherwise reacted to introduce the desired immobilized binding agents. The spools are fed into the guide and pulled through to form a rod bundle with the appropriate spatial arrangement of rod elements. A sheath is applied to the rod bundle as it emerges from the guide and the bundle is either wrapped on a new larger spool or cut into convenient lengths for storage or directly cut into slab arrays. To create a "plus" symbol, a guide with the "plus" configuration in the center (i.e. a cruciform hole) with 4 surrounding areas in each quadrant formed by the "plus" is used. Multiple Rods from spools treated with the appropriate binding agents for a particular assay are fed into the "plus" portion of the guide while multiple non-binding rods are fed into the adjacent guides formed by the 4 quadrants. Of course, preformed bundles of rods (i.e. yarns) could be used to feed the quadrant portions of the array. The process is similar to that described by American Filtrona (Richmond, Va.) and has been given the name "pulltrusion". In this fashion, arrays with binding agents or ink printing distributed in various graphic arrangements can be manufactured.

In another embodiment, the elements of the array are formed by the edges of porous sheet materials, such as microporous membranes. The binding agents are applied or synthesized on the sheet to create binding zones of a given binding agent along the entire edge of the sheet. Alternatively, thin lines of compounds are applied or synthesized to create multiple array elements on a single sheet of material. In this case, each line of immobilized binding agent printed on the sheet is akin to a rod in the aforementioned example. Printing a line of binding agent on the porous sheet results in migration of the agent into the matrix of the material. When the sheet is cut, the impregnated agent in the matrix of the sheet is exposed on the freshly cut edge. The manufactured dimension of the array element is given by the thickness of the membrane material and the width of the line used to apply the compounds. However, depending on the distribution of binding agent within the sheet material the actual dimension of the array element may be smaller, for example, if the binding agent only penetrates ½ the thickness of the sheet. In some special circumstances it may be possible to apply or synthesize binding reagents on both sides of a sheet to further to farther increase array density. After the desired compounds are present on the sheets, the sheets are assembled into stacks or rolls before cutting into individual arrays. Individual arrays are generated by cutting slabs as thin as possible along the Z axis of the roll or the stack. As in the rod format, each array element is incorporated into multiple arrays. Since one dimension of the array element is determined by the sheet thickness, reasonably high density arrays can be obtained even with low density reagent application methods.

An advantage of the printed line format over the rod element format is that the spatial arrangement of the array elements (i.e. printed lines) is fixed along the membrane sheet whereas the rods must be guided to known positions. An advantage of the rod method over the sheet format is that the manufacturing process for the former is compatible with a continuous process while the latter is more suitable to a unit process.

In some cases it may be desirable to use an adhesive compound to bind either the sheets in a stack or the layers of a rolled sheet together to from a cohesive structure. The adhesive used for this purpose must not migrate during the cutting process used to form the individual arrays or else the edges of the sheet material become covered with adhesive and are not accessible to test solutions. Suitable adhesives for binding the sheets are heat activated-double sided DOW Adhesive Films (Dow Chemical, Midland, Mich.). The important features of adhesive selection are: (1) the adhesive does not wet and thereby occlude the pores of the sheet material before and during setting (2) the adhesive sets to a substantially solid consistency that does not migrate and cover the sheet edges during cutting (3) the set adhesive is not brittle and susceptible to cracking when the individual arrays are released from the bundle or roll and (4) the adhesive is stable to the aqueous solvent of the test sample. In general, pressure sensitive adhesives (e.g. SCOTCH TAPE® adhesive, 3M, St. Paul, Minn.) are not desirable because of adhesive migration during mechanical cutting. However, other cutting methods using lasers may allow the use of pressure applied adhesives. One advantage of the roll format over the stack format is that, typically, the compressional forces supplied by the sheath in the rolled structure are sufficient to maintain the integrity of the individual arrays cut from the roll without using any adhesive. This is true for both rod bundles and spiral sheet bundles.

The array is then used to carry out screening tests or diagnostic evaluations. In one procedure, a test sample is exposed to all the array elements by application of a small volume of liquid to the top of the array surface. The liquid is drawn into the array by capillary action. To improve sensitivity, more fluid can be drawn through the array by setting it on an absorbent pad. A washing step can be incorporated to remove unbound components of the test sample from the array. Array elements which have affinity for components of the test sample will retain said components by specific binding events. In a sense, the array acts as a membrane which is composed of short segments of the porous materials used to make the elements of the array. In another procedure, the array is simply soaked in a test sample and the binding reaction proceeds by diffusion of target molecules to the surface of the array or into the matrix of the array. A sample contains the component or components whose binding patterns are to be identified by use of the array. For example, samples may be derived from PCR amplification of materials collected from a human patient, plant or other organism, the products of a combinatorial synthesis, a prospective drug, an antibody or mixture of antibodies, or a volume of blood, plasma, serum or urine. In each case, those skilled in the art recognize the need for the appropriate sample preparation before applying the sample to an array for binding analysis. For example, filtration, centrifugation, or addition of agents to prevent non-specific binding are among the possible operations in preparation of the sample before it is introduced to a diagnostic test.

DETAILED DESCRIPTION OF THE PREFERRED EMBODIMENTS

Figure 1A:
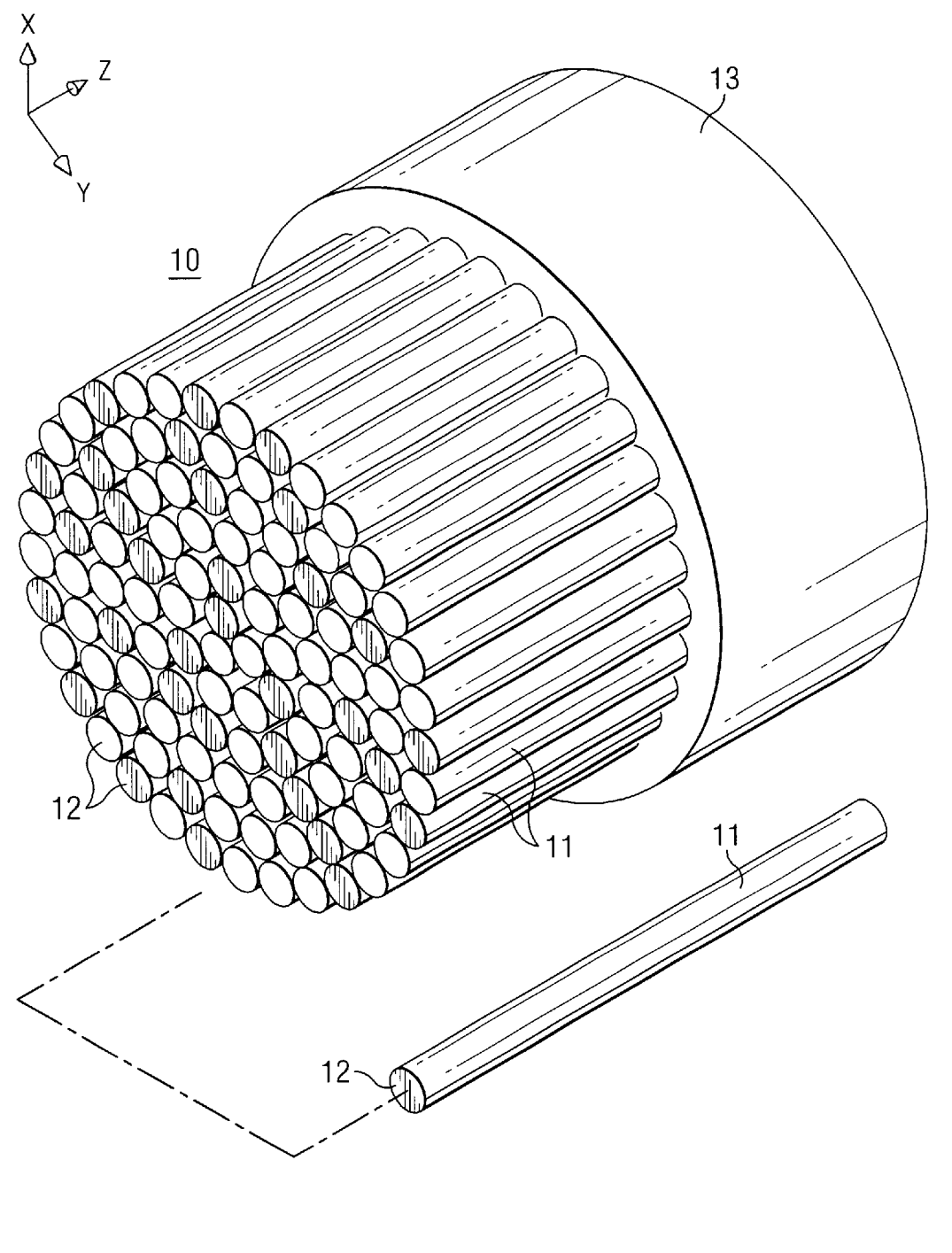
FIG. 1A is a schematic view of the rod bundle 10 consisting of multiple rod elements 11, each with a biological binding properties imparted by immobilization of a suitable binding agent. The bundle is bound and radially compressed about the Z axis with sheath 13. The ends of the rod elements are exposed and regenerated during cutting of the bundle.
Figure 1B:
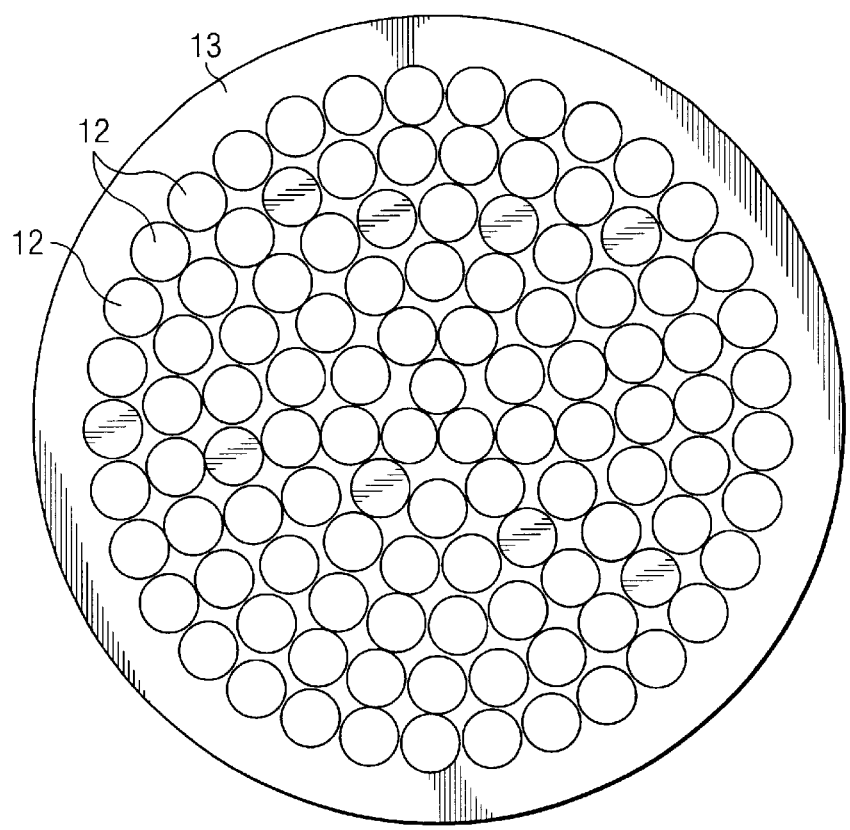
FIG. 1B is an end view of an array cut from bundle 10 showing sheath material 13 and rod ends 12.
Figure 1C:
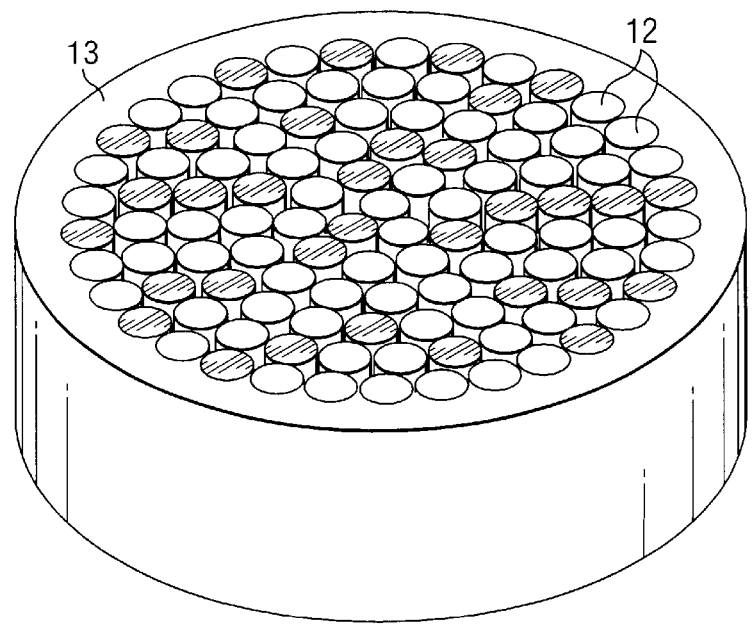
FIG. 1C is a perspective side view of the array cut from bundle 10.
Figure 2A:
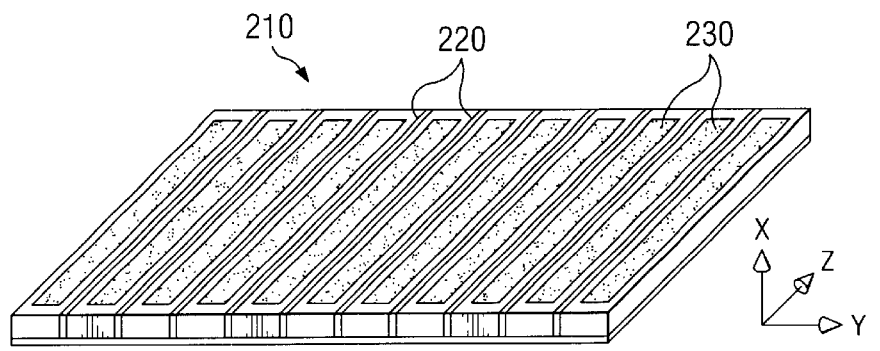
FIG. 2A is schematic view of the sheet material 210 with line of printed binding reagents 230 and lines of hydrophobic ink 220 to form a reagent impregnated sheet 200.
Figure 2B:
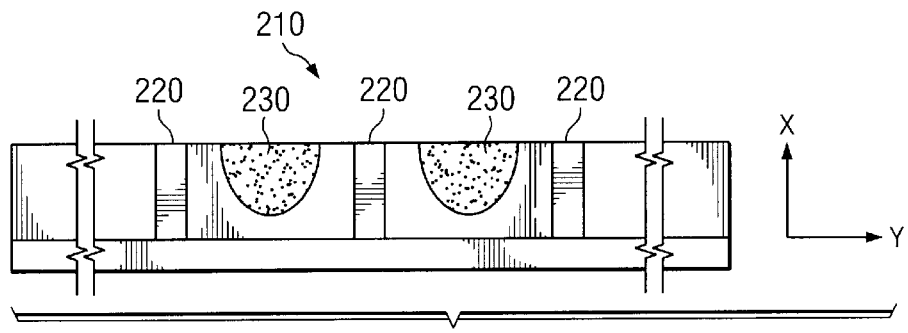
FIG. 2B is an enlarged side view of a small portion of sheet 210 to reveal details of the reagent zones 230 and hydrophobic ink lines 220. Note that the reagents may not extend through the sheet and the distribution within the sheet is dependent on the printing method.
Figure 2C:
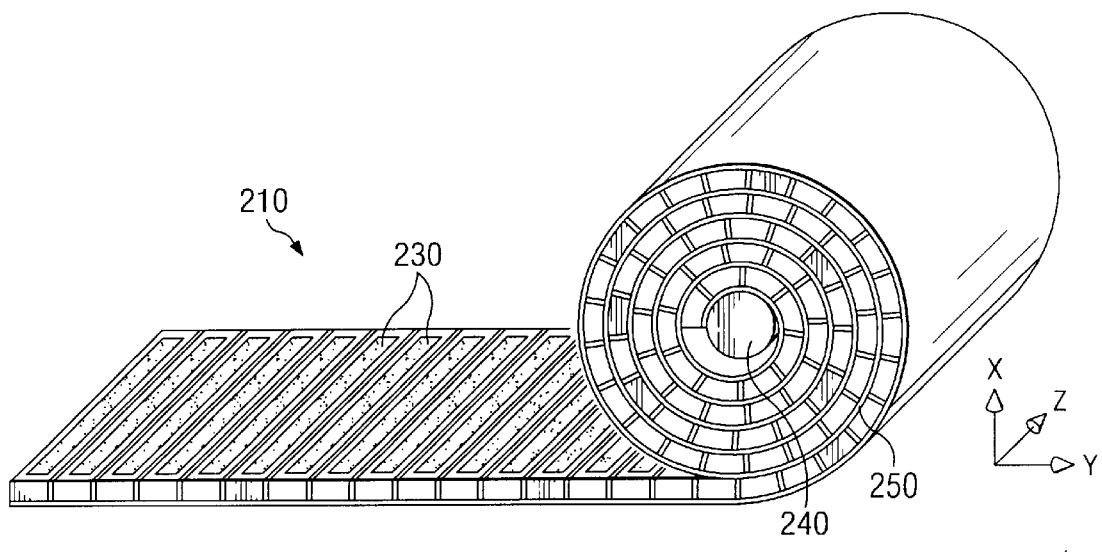
FIG. 2C is a schematic view of the process where by the reagent impregnated sheet 200 is rolled about a cylindrical support 240 to form a spiral wound structure of multiple layers separated by an interstitial space 250 between said layers.
Figure 2D:
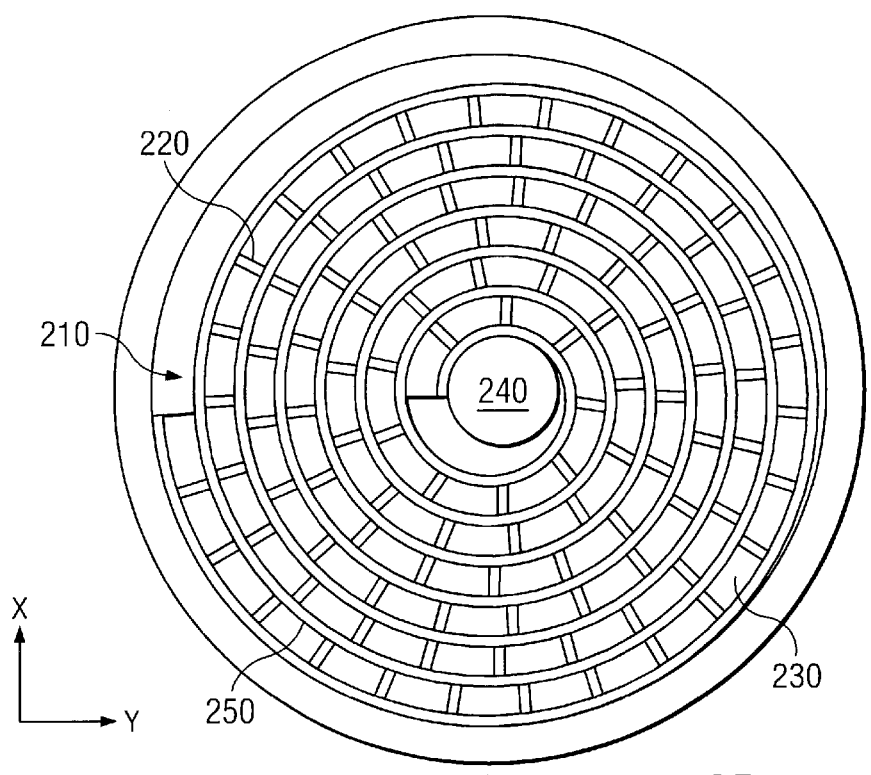
FIG. 2D shows an end view of an array cut from the roll of FIG. 2C after rolling is complete and the stricture is bound with a sheath 260. The array is a spiral structure of multiple layers of sheet material 210 separated by interstitial spaces 250 and wrapped about a core cylinder 240. Each array cut from the bundle is identical with respect to the arrangement of reagent zones 230.
Figure 2E:
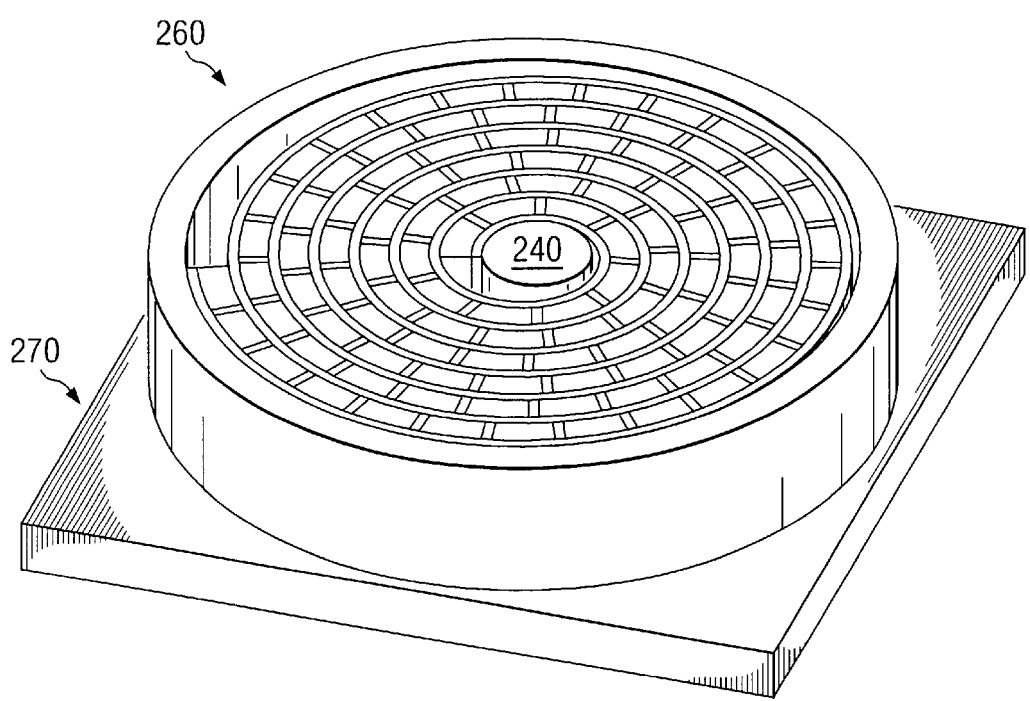
FIG. 2E show a side perspective view of tho spiral array fixed to an absorbent pad 270 to allow liquid to flow through the top of the array and out the distal side into the pad.

A particularly useful application of the invention is the production of arrays derived from cDNA libraries. For example, a sheet of nylon membrane is treated with sodium hydroxide solution to allow binding of DNA samples derived from a cDNA library of M13 clones (Drmanac, R., Electrophoresis, 1992, 13, 566–573). Using a suitable printing method, lines of different DNA samples are applied to the membrane. Reagent jet printing can easily print a line on the sheet or otherwise a pin applicator is used so that multiple dots from the pin overlap to form a line. The different reagent lines on the sheet are formed as close together as possible and with minimum line width allowed by the printing method so that array density is maximized. Reagent jet printing is described in U.S. Pat. No. 4,877,745 and can print lines with a width on the order of 0.001 inch (0.001 inch 0.025 mm=25 microns). In some cases it may be desirable to pre-print identification lines or demarcation lines using insoluble inks when the binding reagents are dissolved in aqueous solutions. Printing of insoluble ink is commonly used to produce grids on microporous membranes used for microbiological analysis and said grid patterns must be water insoluble for use in water analysis (see catalog from Millipore, Bedford, Mass. section on microbial analysis). In some cases it may be desirable to pre-form hydrophobic lines between zones intended for binding agent application. Formation of hydrophobic areas on microporous membrane sheets is commonly used to prevent unwanted intrusion of liquids into membrane edges during testing of bacteriostatic drugs (see catalog from Millipore, Bedford, Mass., Edge-Hydrophobic Membranes).

The array elements formed by drawing lines on a sheet can be identified by several means, viz., (1) spatial arangement and the uniform size of each element (2) use of ink marks to denote the start/stop of a reagent zone or (3) use of identification ink marks printed adjacent to each compound and observed on the edge of the sheet. Ink printed on the surface of porous sheets results in some migration of the ink into the matrix of the sheet. When the sheet is cut, the ink within the body of the porous material is clearly visible, Physical markings such as holes or notches generated by photo-masks and excimer lasers can also substitute for visible ink marks or paints.

Reagent jet printing can also be used to generate combinatorial libraries by chemical synthesis as described in U.S. Pat. No. 5,449,754. For the present invention, the combinatorial method described in U.S. Pat. No. 5,449,754 is used to print lines as opposed to the spots described therein.

After reagent application, the membrane is rolled around a rod shaped supportto form a tight spiral of membrane material similar to a "jelly roll". The outer surface is bound with a material that supplies radial compression (e.g. heat shrink insulation or adhesive tape) and the resulting roll is cut into individual arrays along the Z axis. In this case, the arrays are spiral in nature with each array element formed by the freshly cut edge of the sheet material impregnated with the various binding agents. The support rod can be a hollow tube or a solid cylinder. When a pressure sensitive adhesive is used for the sheath, a few layers of untreated sheet are wrapped on the outside of the spiral to prevent direct contact between the tape and array elements. In this way, the array elements are protected from adhesive migration during cutting.

The process is as follows: printing lines that are 0.1 mm wide (0.1 mm 100 microns) on a membrane that is 0.1 mm thick results in a sheet of membrane with 65536 binding agents with a length of 655 centimeters (i.e. 65536×0.01 centimeters=655 cm 258 inches=21.5 feet). This calculation is consistent with reagent lines that are 100 microns wide and touching one another or reagent lines that are 50 microns wide and delimited on each side by a 50 micron ink line-well within the technical capabilities of current jetting techniques. The binding agents are either synthesized on the solid supports as lines or applied as lines from pre-synthesized materials stored in 384 well microliter plates (170 plates required). When creating such large arrays it may be convenient to divide the sheet into smaller units for printing, on the order of 1 foot long each containing 3,048 reagent lines. The individual sheets can be tested for quality before joining into a 21.5 foot sheet for assembly of the spiral bundle.

An automated device to apply the multitude of reagents to a 21.5 foot sheet is assembled from an X-Y-Z table (e.g. Asymtek) fitted with a reagent dispenser, a step motor controlled take up spool and an adjustable drag pay-out spool. The roll of membrane is mounted on the pay-out spool, fed though guides on the X-Y-Z table surface and attached to the take-up spool. The X-Y-Z table is used to pick up the reagents from the 384 well micro-titer plates using a dispensing device (e.g. an 8 tip pipette) and draw lines across the sheet of membrane. The membrane can be pre-printed with the identification/zone isolation lines or this step can be carried out upstream of the reagent application. After the reagent lines are drawn, the take-up spool is incremented to advance the membrane sheet and the printing process is repeated using the appropriate sheet advancements.

After all reagents are applied the take-up spool is bound and cut into individual arrays.

The width of the sheet (Z axis) is determined by the number of arrays to be generated of a given thickness. The number of arrays obtained from a spiral bundle is given by the sheet width divided by the thickness of the individual arrays. The 655 cm long sheet is rolled around a 0.5 outer diameter tube (e.g. plastic straw) to form a spiral roll with about 121 turns whose outer diameter is surprisingly only about 3 cm or 1.15 inches. The outer diameter of the spiral bundle can be calculated by noting the surface area of the bundle and dividing by the surface area of an individual array element multiplied by the number of array elements. That is, 65536 elements multiplied by the element array (0.01 cm×0.01 cm 0.0001 cm2) gives a total area of 6.6 cm2 which is equal to the area of a circle 3 cm in diameter (pi r2=6.9 cm2) minus the area of the 0.5 cm core (pi r2=0.2cm2). Improvements in spatial density of the array are realized by decreasing the membrane thickness and reducing the width of the reagent lines. Using a membrane that is 10 microns thick (10 microns=0.01 mm=0.001 cm) the outer diameter of the 21.5 foot spiral wound bundle is only 1 cm with a 0.5 cm core, Alternatively, the printing could be carried out on commercially available membranes which are 100 microns thick and after printing the membrane thickness reduced to 10 microns by mechanical compression using rollers. Of course, such a process would substantially reduce the pore size of the membrane and may not permit the use of large labels like colloidal gold or selenium colloid. The spiral is bound and then cut along the z axis (i.e. the membrane sheet width) to create individual arrays with identical zones of immobilized bindings agents. Thinner array slabs will yield more arrays from a given bundle. Cutting by hand can easily give arrays 1 mm in thickness so that a 8 inch (20 cm) wide sheet yields 200 arrays for each bundle. More sophisticated methods of cutting (e.g. laser light) could yield arrays of 0.2 mm in thickness and increase this number to 1000.

Attachment of pre-synthesized binding agents can be carried out in a variety of ways both by adsorption or by covalent attachment. Nitrocellulose has a natural affinity for proteinaceous materials like antibodies and the material can be directly applied and immobilized by adsorption. For DNA, a number of commercially available membrane products exist for covalent linkage. For example, IMMOBILON membrane (Millipore), or BIODYNE C membrane (Pall Biosupport, Glencove, N.Y.) have been used for covalent immobilization of small nucleic acids (10–20 bases) via an amino group added during synthesis. Alternatively, large DNA molecules can be covalently linked to nylon membranes using an ultraviolet light box, for example, STRATA-LINKER light box (Strategene, La Jolla, Calif.). The main requirement of the porous material used for immobilization is that it allow some of the binding agent to penetrate into the matrix, i.e., more than pure surface deposition. In addition, since the matrix of the material forms the binding zones of the array a substantially uniform membrane is desired. For this reason, membranes with a highly asymmetric structure or which contain embedded fabrics are less desirable for the present invention than uniform membranes.

Reacting an entire sheet or rod element by dipping into a container of chemical solution is a convenient method of producing compounds by combinatorial synthesis. For example, all possible 4-mer DNA sequences would require a "book" of 44=256 sheets or pages. Page size is selected to allow convenient handling by hand or machine. The pages are placed into tubes with the appropriate connections on each end to substitute in place of the standard glass bead columns of a commercially available DNA synthesizer (e.g. Applied Biosystems, Foster City, Calif.). In the first step, groups of 64 pages are reacted with each base A, T, G, and C. Next step, 64 page books are made by combining 16 pages from each of A, T, G, and C piles. The new books are reacted with A, T, G, and C to form all possible dimers (16 in all), each duplicated 16 times. Next step, 4 new 64 page books are made from the dimer pages, i.e., AA, AT, AG, AC, TA, TT, TG, TC, . . . CC. At this phase, each of the 4 new books are identical and contain 64 pages made up of the 16 different dimers each duplicated 4 times. The 4 books are reacted wit A, T, G, and C to form all 64 possible trimers. The last 4 books are assembled from the trimer pages, each book identical and each trimer page present only once. The final A, T, G, or C base is added to each book and all are combined to form the 256 page book of all possible 256 sequences of 4-mer DNA with a unique sequence on each page. The book could be cut into several books of smaller width/height with each having all 256 of the 4-mer sequences. Alternatively, the pages of the book can be held together in a stack using a glue, bonding material, or mechanical device to from a solid stack of pages which are then cut in the z-axis to create one dimensional arrays formed by the edges of the pages. Alternatively the pages can be rolled into a spiral array type structure using several pages instead of just one as described above and arrays generated by cutting slabs. The mechanics of combinatorial synthesis using a flat sheets or rods of material are the same as those described by U.S. Pat. No. 5,175,209 with the flat sheets or rod elements replacing the porous wafers as the substrates for synthesis. The book format can attain reasonable spatial densities by using thin sheet materials, e.g., track etch polyester or polycarbonate membranes are only 10 microns thick so that 1000 pages combine to give a book only 1 cm thick.

The sheet or rod materials must be compatible with the reagents used during organic synthesis. Typically glass particles or cross-linked polystyrene particles are used in standard DNA synthesis with phosphoramidite chemistry and the solvents acetonitrile, dichloromethane, and tetrahydrofuran are present. Hence, a likely candidate for the present invention is an EMPORE® sheet, a sheet of chemically bonded silica particles suspended in a web of polytetrafluoroethylene (PTFE) microfibrils, i.e., both silica and PTFE are resistant to the chemicals used in DNA synthesis (EMPORE® is a trademark of 3M, Minnesota and the material is available from Analytichem International, Harbor City, Calif.). Another possible support is cross-linked polystyrene in sheet form instead of micro-particle form. In this case a thin sheet of polystyrene would be treaded in the same fashion as the microporous styrene particles to obtain a cross-linked solvent stable structure. Alternatively, the cross-linked polystyrene beads could be incorporated into an EMPORE sheet type material. Another material that has excellent resistance to organic solvents is microporous PTFE available from Millipore under the names FLUOROPORE® and MITREX®. Since these material do not have the required functional groups to carry out solid phase organic synthesis they would have to be surface modified, for example, by using a procedure described in U.S. Pat. No. 4,974,002. A microporous membrane with the required solvent resistance and functional groups for solid phase organic synthesis is hydrophilic DURAPORE® membrane, also available from Millipore. Surface modified polypropylene membranes are also used for solid phase synthesis of oligonucleotides (Matson, et al. Analytical Biochemistry 1994, 217, 306–310). Finally, microporous glass in sheet or rod configurations are available from Asahi Glass America, Inc. N.Y., N.Y. in a wide range of pore sizes from 0.008 micron up to 5 micron. While this material would be most suitable for DNA synthesis, clearly, the brittle nature of the porous glass sheet would not be compatible with the spiral bundle and the rod bundle would be required. A final option is to synthesize the binding agents on standard supports, i.e., microporous glass particles, and immobilize the particles in the porous material by physical trapping/filtration. In this way the material does not have to be exposed to the organic solvents used in synthesis.

Identification of the array elements that generate positive or negative label reactions is accomplished by noting the positions of rods or sheet elements. However, in some cases it may be desirable to synthesize a number of compounds at random. In cases where a very large numbers of compounds are to be generated, a random or Monte Carlo type approach is suitable. For example, if all possible pentipeptides of say, 20 different amino acids are to be generated then an array would require 20$^5$=3,200,000 elements (or probe sites on an array); a difficult and large number of elements to screen for binding. In a statistical approach we randomly sample 5000 of the possible 3,200,000 combinations. The first 20 bundles would contain 250 rods reacted with each of the 20 amino acids and marked accordingly. The rods would then be combined and "shuffled" as in a deck of cards. Shuffling could be carried out manually or using electronically generated random numbers. The second set of 20 bundles would be formed by "dealing" out 20 piles from the rods of the first synthesis. Each bundle is reacted with one of the 20 amino acids and then combined for shuffling and dealing. At the end of 5 cycles a random sampling of 5000 peptides from the 3,200,000 possible peptides is generated for testing. Any binding motif established by the random experiment would help to narrow the search and allow for a complete search of a subset of the 20 amino acids. Of course, this approach would find most utility when the number of combinations is even greater than the example presented here.

Marking the rods can be accomplished by paints or physical marks. For example, after each step of synthesis, the bundle of rods is dipped in a paint at one end. Spin coating the paint forms a thin zone of paint for later identification of the synthesis step. Different colors are used to identify the sequence such as red=adenine, blue=guanine, yellow=cytosine and green=thymine in DNA synthesis. At the end of synthesis, each rod element is coated with a series of paints that represents the sequence of synthesis steps. The series of bands are revealed by cutting a rod and examination in a microscope to give the spatial distribution of the elements in all arrays in the bundle. Note that individual rods must preserve their spatial arrangement throughout the Z-length of the bundle. If exposed to the organic chemicals of a synthesis, the paint must be compatible and resistant to the solvents used during synthesis. In most cases of organic synthesis, an epoxy or silicon based paint that chemically cross-inks during curing is suitable provided strong acids or oxidizing agents are avoided. In this regard, marking by physical damage using laser ablation methods has certain advantages.

A large number of formats can be used to detect which elements of the array have bound components from the test mixture. If high density arrays are not needed, the target molecules can be radioactively labeled with P32 and array binding detected using autoradiography. Unfortunately, the spatial resolution of P32 autoradiography is not sufficient for use with high density arrays with elements on the order of 10 microns and other methods are needed. Other methods using either direct or indirect labeling with enzymes or flurophores are possible. For a comprehensive discussion on methods of detection and assay formats such as sandwich assays or competition assays refer to Pierce Catalog and Handbook 1994. For example, the target molecules of the test sample can be labeled with biotin or a biotinylated antibody with affinity for the target molecule can be used for the same purpose. Subsequent binding of target components to the array elements results in a localized accumulation of the biotin moiety. The array elements containing the biotin label are revealed using standard enzymatic chemistries to generate colorimetric, fluorigenic, or luminescent based signals. For example, avidin labeled alkaline phosphatase will bind to biotin and a visible dark blue signal generated by the action of alkaline phosphatase on BCIP+NBT (5-bromo-4-chloro-3-indolyl phosphate and nitro blue tetrazolium). Other enzyme-substrate combinations can be used to generate fluorescent and luminescent signals. Alternatively, avidin, streptavidin, or antibodies which bind biotin can be directly labeled with a fluorphore (e.g. fluorescein) or a microparticle dye (e.g. gold colloid or selenium colloid as in U.S. Pat. No. 5,120,643) and exposed to the array to develop a signal. Another option is to use labeled secondary antibodies which directly bind to the target molecule to carry out detection as in a sandwich assay format. In cases where flow through the array is needed to improve sensitivity, the porous rod or sheet materials must have a pore size sufficiently large to allow entry of the label into the matrix, otherwise the label reaction is confined to the rod surface. Flow through the array is especially desirable when colloidal labels are used to generate the signal.

Cutting the rod or spiral bundles to form the arrays can be accomplished using mechanical or laser methods. Razors or knife blades can be used to manually cut porous polymeric materials to give arrays 0.2–1 mm thick. A microtome device is able to cut thin sections of various materials for microscopic evaluation and may be useful for array generation. The samples used in such a device are usually biological in nature and derived from tissue samples, for example, a tumor surgically removed from a patient. Typically, the sample preparation for cutting thin sections with a microtome makes use of paraffins or plastic embedding media. The thin section is then "stained" using the specific interactions generated by antibody binding followed by staining with antibody coated collodial gold, or followed by staining with antibody coated collodial gold, or "IMMUNOGOLD" stain (Ted Palla, Inc. Redding, Calif.) or the variety of enzyme/substrate combinations described above that generate fluorescent or visible colors that can be observed with a suitable microscope. In the present invention, the rod or spiral arrays could be subject to the same manipulations when flow through the array is not required for signal development. Within this context, the array becomes analogous to the tissue sample with the various elements of the array available for binding with antibodies or nucleic acids or other specific interactions known to those skilled in the art. To summarize: prior art in the area of microscopy support the concept that the arrays can be cut very thin using mechanical means and that the array elements are able to bind biological agents even when that are embedded in a paraffin or plastic compound that helps to support the specimen during mechanical cutting.

Both the rod bundle and spiral bundle arrays are surprising stable to handling. In the case of rod bundles formed from glass or ceramic materials a fine abrasive diamond or carborundum blade is applicable to cut arrays. It may be possible to use more sophisticated cutting methods using CO2 or excimer lasers provided the compounds on the cut edge are not damaged by heat generated during the process. CO2 lasers are frequently used in the clothing industry to cut multiple layers of cloth or synthetic fabrics without damage from heating. Excimer lasers are used in eye surgery and since the process is photo-ablation, there is little damage to the surrounding tissue. Both methods may prove useful in cutting arrays from the spiral or rod bundles.

In summary, the invention is directed toward the detection of components in a sample mixture or detection of compounds on an array by:
 a) immobilizing binding compounds onto rod shaped array elements;
 b) forming a bundle of the rod elements using a guide to create a spatially uniform arrangement of rod elements and securing with a sheath material;
 c) cutting individual arrays from the bundle to generate a multiplicity of binding surfaces and fixing or placing one side of the array to an absorbent pad;
 d) applying a sample to the surface of an array and allowing the sample to flow through the porous rod elements of the array into the absorbent pad;
 e) applying a washing solution to remove unbound compounds of the sample mixture;
 f) applying a labeled compound that binds to the components of the sample mixture which are bound to elements of the array;
 g) washing away unbound label and observe binding pattern directly or by application of a reagent to allow detection of the bound label.
 h) correlating the binding pattern of the binding surfaces with the composition of elements in the array.

The invention is directed toward the detection of components in a sample mixture or detection of compounds on an array by:
 a) forming lines of immobilized binding compounds on a sheet of material, wherein lines of binding compounds maybe separated by identification marks, and the binding material is impregnated into the thickness of the sheet material;
 b) rolling the printed sheet into spiral wound structure about a rod and securing roll with a sheath;
 c) cutting individual arrays from the bundle to expose binding elements formed by the freshly exposed edge of sheet material separated by identification marks and interstitial space between adjacent membrane layers, and fixing or placing one side of the array onto an absorbent pad;
 d) exposing and develop the array as in e-h above;
 e) correlating the binding pattern on the array with the composition of the binding elements.

The invention is directed toward the detection of components in a sample mixture or detection of compounds on an array by:
 a) synthesizing of binding compounds onto rod shaped array elements using a randomized method;
 b) marking the identification of each rod at each synthesis step by spin coating with paint;
 c) forming a bundle of the rod elements and securing with a sheath material;
 d) exposing and developing the array as in e-h above;
 e) correlating the binding events with the identification marks.

The invention is directed toward the detection of components in a sample mixture or detection of compounds on an array by:
 a) immobilizing binding compounds onto rod shaped array elements;
 b) forming a bundle of the rod elements and securing with a sheath material so that rod elements treated with a given binding agent are grouped to create a graphic symbol/s surrounded by rod elements with different or substantially no affinity for components in the test sample;
 c) cutting individual arrays from the bundle and fixing or placing one side of the array to an absorbent pad;
 d) applying a mixture of sample and label to the surface of an array, allowing the mixture to flow through the porous rod elements of the array into the absorbent pad and form attachments between the label, analyte and immobilized binding agent as in a "sandwich assay" format;
 e) washing away unbound label and observe binding pattern directly or by application of a reagent to allow detection of the bound label;
 f) correlating the graphic symbol/s with the presence or absence of analyte(s).

EXAMPLE 1

A bundle of rods (spun polyester sewing thread, Lily, USA) some treated with the protein bovine serum albumin (BSA) and some not treated were gathered into a bundle and placed into heat shrink tubing and radially compressed. The BSA treatment consisted of soaking the rod in a solution of about 1 mg/ml BSA for 5 minutes, washing with distilled water for 5 minutes and air drying. Polyester rods treated in this fashion adsorb BSA throughout the porous matrix. The resulting bundle was cut into slabs about 1 mm in thickness to form arrays, Each array contains a section from all the rod elements. A solution of selenium colloid, a micro particle that binds to bovine serum albumin, was placed on top of the array of porous rods. A piece of absorbent paper was placed under the slab to draw the liquid through the array. After liquid was drawn through, the protein coated rods were clearly visible by a red color. The array of porous rods acts like a membrane of porous material but consists of a myriad of different zones each of which can have different binding properties.

EXAMPLE 2

Identification marks on individual rods were produced by spin costing. Rods of porous polypropylene were dipped into acrylic paint, fixed at the opposite end to a motor shaft with tape, and spun at approximately 1000 RPM to remove excess paint. The process was repeated using different color paints to identify a given DNA base in the process of synthesis. The paints were allowed to dry 1 minute between applications while spinning. After the last paint application a bundle of rods was formed and cut to reveal the layers of paint on each rod. Using a 10X stereo microscope it was possible to read the colors of the different layers of paint exposed by cutting the bundle and thereby identify the sequence of reaction steps for each rod.

EXAMPLE 3

Figure 3A:
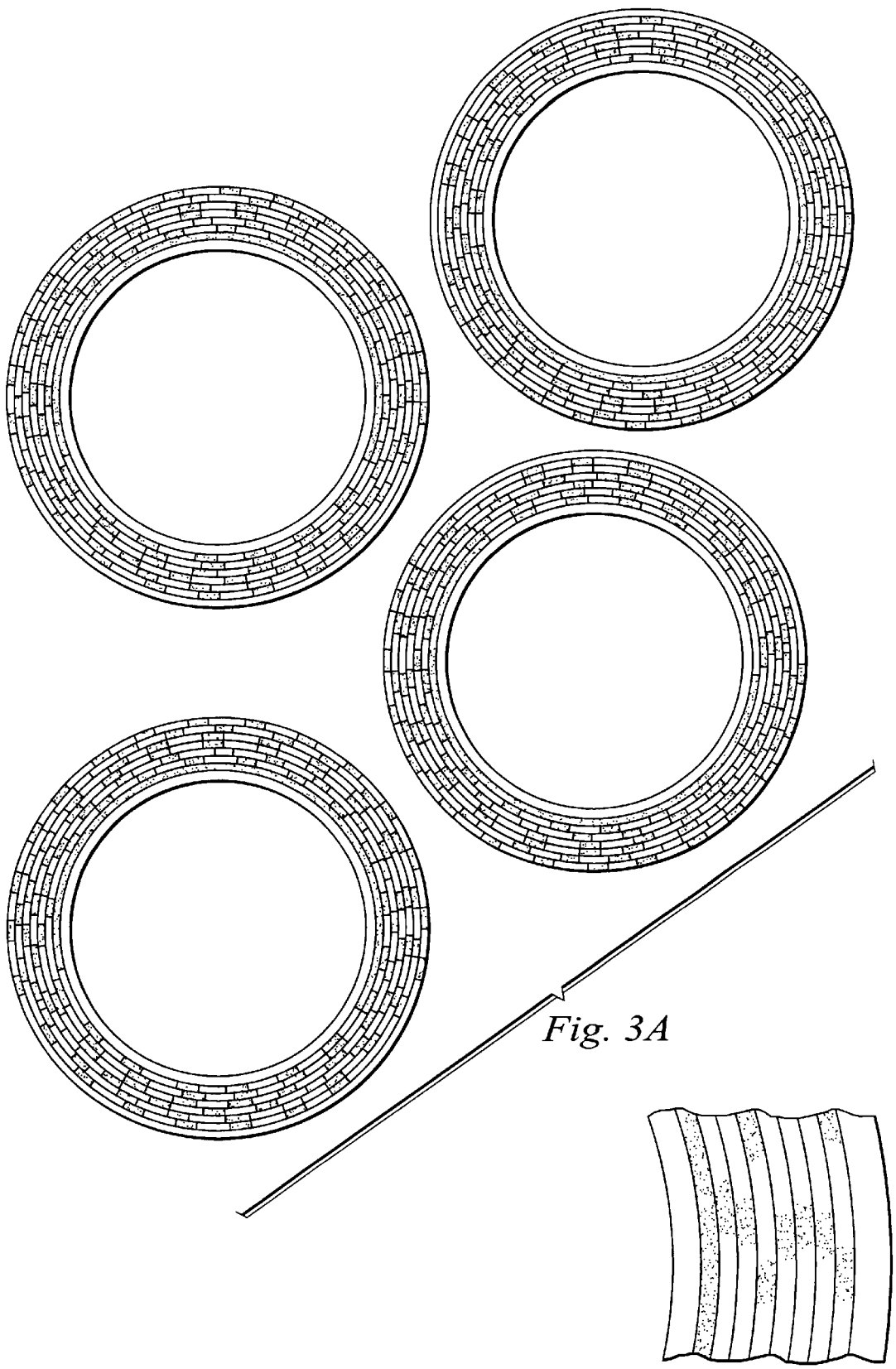
FIG. 3A shows a laser printer image of 4 arrays generated by the process described in Example 3. The arrays were placed on a scanner and scanned at 600 dpi with 256 gray levels and the data stored as a TIFF file.
Figure 3B:
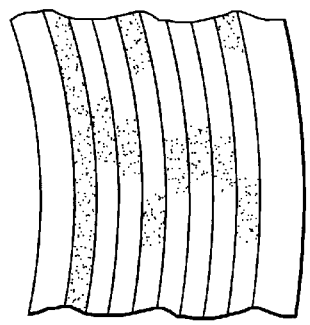
FIG. 3B shows an enlarged image of a small section from one array of FIG. 3A.

Reagent demarcation lines were printed onto a sheet of 5 micron nitrocellulose membrane about 6 inches long and 3 inches wide using an Style Writer U (Apple Computer, Cupertino, Calif.) thermal ink jet printer. The ink lines were about 1 mm wide and separated by about 2 mm spacing. After printing, the sheet was rolled tightly by hand around a plastic straw, and bound with adhesive tape. The spiral bundle was placed inside a metal tube whose inner diameter was slightly larger than the outer diameter of the bundle. The a 1–2 mm length of the bundle was allowed to extend from the end of the metal tube and an array slab was cut with a razor blade using the metal tube as a guide to obtain a uniform straight cut. FIG. 3 shows a laser print of the 256 gray level image of the array obtained by placing the array on an Epson ES-600C scanner. Each array has in inner diameter of 0.6 cm, an outer diameter of 0.9 cm and contains approximately 160 array elements, i.e., spaces between the ink marks. Microscopic examination showed the ink penetrated about ½ to ¾ through the 0.1 mm thickness of the membrane. As a result, each array element defined by the space between each pair of printed lines was clearly visible under a microscope. The arrays were surprisingly stable and easily handled even though the layers of the spiral are only held in place by compression between the central rod (straw) and the outer sheath (adhesive tape). Arrays as thin as 0.2 mm were cut by hand, albeit, not uniformly. The reagents would be applied to the spaces between the lines. Since the standard ink for this printer is water soluble, reagents would have to be applied in a non-aqueous solvent that does not dissolve this ink or affect the membrane.

EXAMPLE 4

Lines of BSA were printed by hand on 0.1 mm thick 5 micron pore nitrocellulose membranes using a reagent pen device and a ruler. The lines were about 0.5 mm wide and placed at random spacing along the 6 inch length of the membrane. The resulting sheet was rolled, bound and cut as in Example 3. The arrays were placed on a pad of adsorbent material (i.e. a paper towel) and a solution of selenium colloid applied to the top of the array. The colloid solution formed an annular shaped drop on the array surface and was adsorbed by the spiral membrane of the array. Once the array was saturated, colloid solution began to flow into the underlaying absorbent pad. When excess liquid on top of the array was depleted, flow stopped. Flow of colloid solution could be re-started by applying more solution to the top of the array. In this way, about 0.5 ml of colloid solution was drawn through the array. The array elements formed by the lines of BSA were clearly visible as dark red bars with dimensions of 0.5 mm×0.1 mm, at various locations throughout the spiral array.

Figure 4:
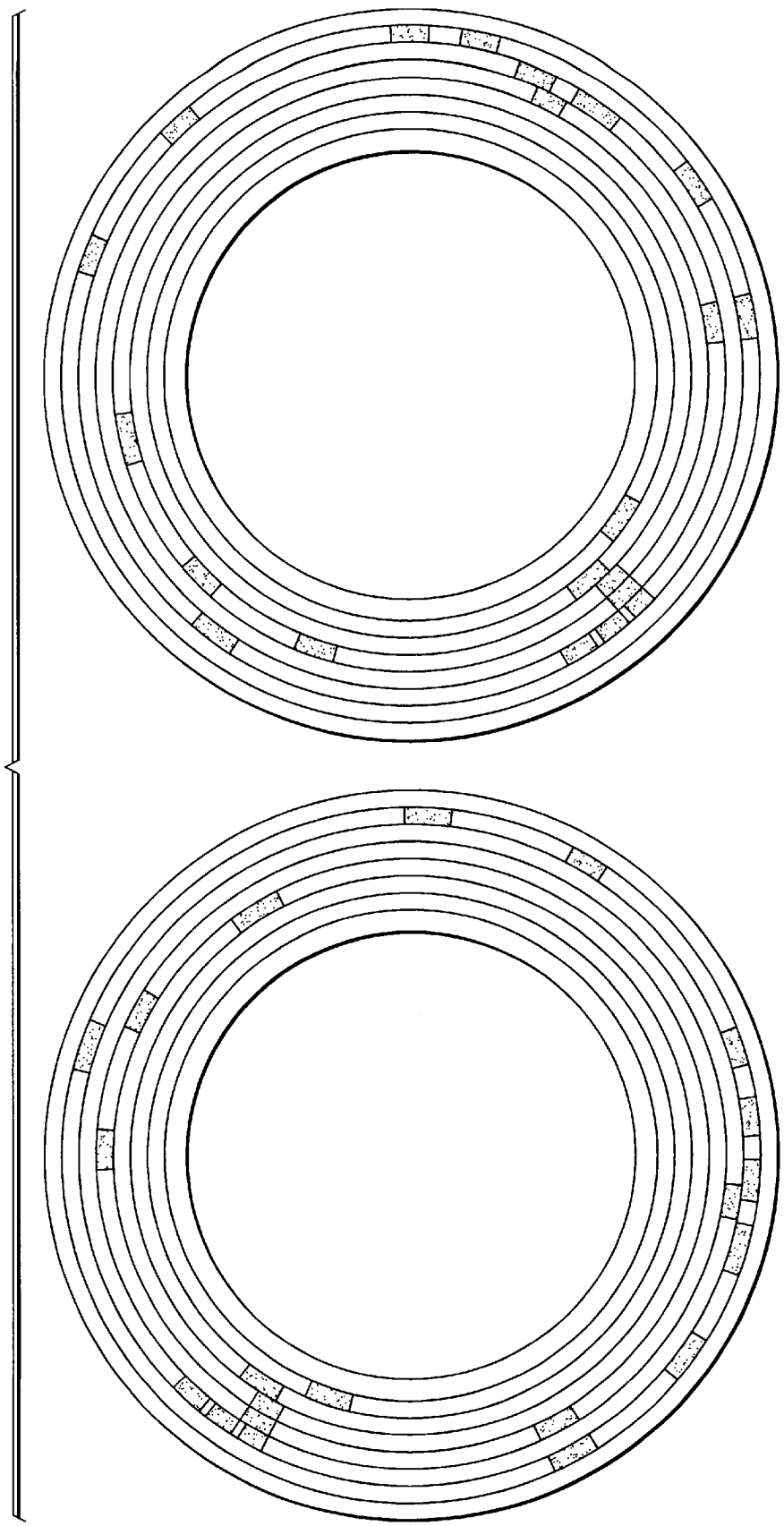
FIG. 4 shows a laser printed image of 2 arrays generated by the process described in Example 4. The image files were generated at described in FIG. 3A.

Visibility of the BSA zones could be enhanced by washing the array by applying distilled water and letting it draw through the array until the background red color was gone. FIG. 4 shows a laser printer figure of the 256 gray level image of the array obtained by placing the array on a scanner.

EXAMPLE 5

Procedures described in this example are taken from Zhang, et al., Nucleic Acids Research, VI. 19, No. 14,3929–3933. Probes that recognize normal and mutation sequences of the cystic fibrosis (CF) gene are synthesized with "aminolinkers". The probes are 21 bases in length with a primary amino group on the 5' end. As many as 300 mutations are known for the CF gene so an array may contain 600 such probes with Y2 representing the normal sequence and Y2 representing the mutation sequence. BIODYNE C membranes (Pall Biosupport, N.J.) are rinsed with 0.1 N HCl then treated with freshly prepared 20% (1-Ethyl-3-(Dimethylamino propyl) Carbodiimide hydrochloride) in deionized water and rinsed with deionized water. The probes are applied to the BIODYNE C membrane as prescribed in a BIO-DOT apparatus (Bio-Rad, Calif.) with the exception that the apparatus is modified to form lines instead of spots. The amino-modified oligonucleoties are applied to the activated membrane in 0.5 M sodium bicarbonate buffer pH 8.4 for 15 minutes. The lines are rinsed with tris buffered saline and 0.1% Tween (Sigma, Mo.). Remaining active groups are quenched with 0.1 N NaOH for 10 minutes. The filters are rinsed with deionized water and air dried. Membranes are then rolled about a plastic support 0.5 cm in diameter to form a spiral bundle, bound and sliced into arrays. Detection of CF mutations is performed on biotinylated PCR product from patient samples. The PCR products are denatured with 0.25 N NaOH and hybridized to the arrays in 5×SSPE with 0.5% sodium dodecyl sulfate (1×SSPE=180 mM NaCl, 10 mM NaH2PO4, 1 mM ethylene diamine tetraacetic acid, pH 7.2). Sample is applied to the top of the array and allowed to flow through the array into an underlaying absorbent pad for 30 minutes at 45° C. The required incubation times can be obtained by adjusting the pore size of the absorbent pad, using small amounts of pad, or using intermittent contact with the absorbent pad. The arrays are washed with 2×SSPE, 0.1% SDS at 45° C. for 15 minutes to remove unbound target. Streptavidin-horse radish peroxidase (5 mg1ml, Cetus) in 2×SSPE and 0.1% SDS is drawn through the array for 15 minutes and then washed with the same buffer for 10 minutes. A luminescent signal is generated by flowing a mixture of equal volumes of ECL Gene Detection reagents A+B (Amersham, Ill.) through the array for 1 minute and applying the arrays to a HYPERFILM-ELC sheet (Amersham, Ill.) for a few seconds or minutes.

The signal appears as a dark spot on the film and the array pattern indicative of the genetic composition of the patient sample.

EXAMPLE 6

Lines of biotinylated BSA solution (2.5 mg/ml) were drawn on 5 micron nitrocellulose membrane using a reagent pen device. The finest lines obtained by this method were 100 microns in width. The membranes were rolled, bound and cut into slab arrays and placed on a paper towel. A solution of 1% casein and a 1:10,000 dilution of alkaline phosphatase-avidin conjugate (EXTRAVIDIN®) conjugate, Sigma Chemical, St. Louis) in 20 mM Tris, pH 7.5 was applied to the top of the array and allowed to flow through. The array was then soaked in BCIP/NBT (Sigma FastTM5-bromo-4-chloro-3-indolyl phosphate/nitro blue tetrazolium) for 10 minutes. Dark purple zones formed at the array sites where biotinylated BSA was applied.

While certain features and embodiments of the invention have been shown and described in detail herein, it will be understood that the invention encompasses all modifications and enhancements within the scope and spirit of the following claims.

What is claimed is:

1. An array bundle for use in detecting predetermined components in sample mixtures, comprising:
    a plurality of longitudinally oriented cells;
    a first binding compound disposed in a first cell, the first binding compound being specific to a first component to be detected from the sample mixtures;
    a second binding compound disposed in a second cell, the second binding compound being specific to a second component to be detected from the sample mixtures, wherein the binding compounds are impregnated into a sheet to form the cells, and the sheet is wound around a cylindrical support to form a bundle; and
    a sheath surrounding the cells to hold the bundle together, wherein the bundle is cut transversely to form a series of identical arrays of cells, each array being used with a single sample mixture.

2. The array bundle of claim 1 wherein the cells are defined between lines of hydrophobic ink.

3. An array bundle for use in detecting predetermined components in sample mixtures, comprising:
- a sheet impregnated with binding compounds specific to components to be detected from the sample mixtures, wherein each of the binding compounds is applied to the sheet to define a plurality of longitudinally oriented cells, the sheet being wound around a support to form a bundle; and
- a sheath surrounding the cells to hold the bundle together, wherein the bundle is cut transversely to form a series of identical arrays of cells.

4. An array bundle for use in detecting predetermined components in sample mixtures, comprising:
- a plurality of longitudinally oriented cells;
- a first binding compound impregnated into a sheet to form a first cell, the first binding compound being specific to a first component to be detected from the sample mixtures; and
- a second binding compound impregnated into the sheet to form a second cell, the second binding compound being specific to a second component to be detected from the sample mixtures; and
- the sheet being wound around a cylindrical support to form a bundle of cells and the bundle being cut transversely to form a series of identical arrays of cells, each array being used with a single sample mixture.

5. The array bundle of claim wherein the cells are defined between lines of hydrophobic ink.

* * * * *